(12) United States Patent
Yamamoto et al.

(10) Patent No.: US 6,677,123 B1
(45) Date of Patent: Jan. 13, 2004

(54) PROCESS FOR DETECTING INCREASED RISK OF FETAL CHROMOSOMAL ABNORMALITY

(75) Inventors: Ritsu Yamamoto, Sapporo (JP); Shinji Satomura, Osaka (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/241,085

(22) Filed: Feb. 1, 1999

(30) Foreign Application Priority Data

Feb. 3, 1998 (JP) ............................. 10-038186

(51) Int. Cl.[7] ................... G01N 33/543; G01N 33/53; G01N 33/74
(52) U.S. Cl. ................. 435/7.1; 935/7.21; 935/7.24; 935/7.25; 935/7.93; 435/7.9; 435/40.5; 435/973; 436/63; 436/65; 436/87; 436/86; 436/501; 436/510; 436/518; 436/519; 436/520; 436/524; 436/536; 436/811; 436/814; 436/817; 436/818; 436/827; 436/906; 530/388.7; 530/389.6; 530/412; 530/413
(58) Field of Search ................... 435/7.1, 7.93, 435/18, 973, 7.9, 7, 7.21, 6, 91.2, 7.24, 7.25, 40.5; 436/501, 510, 63, 570, 906, 811, 814, 65, 817, 518, 536, 87, 818, 86, 827, 519, 520, 524; 530/412, 413, 389.6, 388.7; 536/24.31, 25.4; 935/77, 78

(56) References Cited

U.S. PATENT DOCUMENTS

| | | | | |
|---|---|---|---|---|
| 5,252,489 A | * | 10/1993 | Macri | 436/87 |
| 5,506,150 A | * | 4/1996 | Canick et al. | 436/510 |
| 5,591,589 A | * | 1/1997 | Katoh et al. | 435/7.1 |
| 5,641,628 A | * | 6/1997 | Bianchi | 435/6 |
| 5,714,325 A | * | 2/1998 | Bianchi | 435/6 |

FOREIGN PATENT DOCUMENTS

| | | | |
|---|---|---|---|
| EP | 0 653 640 | 5/1995 | |
| JP | 2-5895 | 1/1990 | |
| JP | 8-500181 | 1/1996 | |
| JP | 2525474 | 5/1996 | |
| WO | WO 91/07660 | * 5/1991 | ......... G01N/33/53 |

OTHER PUBLICATIONS

Shimizu et al., "Comparison of carbohydrate structures of serum alpha–fetoprotein by sequential glycosidase digestion and lectin affinity electrophoresis.", Clinica Chimica Acta, vol. 254, 1996, pp. 23–40.*
Katoh et al., "Analytical Method for sugar chain structure involving lectins and membrane ultrafiltration.", J. Biochem, vol. 113, pp. 118–122, 1993.*
Taketa et al., "A collaborative Study for the evaluation of lectin–reactive alpha–fetoprotein in early detection of hepatocellular carcinoma.", Cancer Research, vol. 53, pp. 5419–5423, Nov. 15, 1993.*
Simpson et al., "Isolating fetal cells from maternal blood.", JAMA, Nov. 17, 1993–vol. 270, No. 19, pp. 2357–2361.*
Spector et al., "Properties of fetal and adult red blood cell arginase . . . ", Am J Hum Genet 32:79–87, 1980.*
Suzumura S., "Prenatal diagnosis of chromosome abnormalities with special reference to amniotic fluid and serum alpha–fetoprotein concentrations.", Keio Igaku (1992), 69(3), 485–497.*
Arab et al., "Maternal serm beta humna chorionic gonadotropin combined with materal serum alpha–fetoprotein appears superior for prenatal screening Down syndrome than either test alone.", American Journal of Human Genetics, vol. 43, No. 3, Sep. 1988, p. A225.*
Chemical Abstracts, vol. 117, No. 15, Oct. 1992, Abstract No. 146666, XP002104693.
MEDLINE, Abstract No. 93203166, XP002104691.
Chemical Abstracts, vol. 120, No. 5, Jan. 1994, Abstract No. 51400, XP002104694.
Chemical Abstracts, vol. 125, No. 21, Nov. 1996, Abstract No. 268643, XP002104692.

* cited by examiner

Primary Examiner—Long V. Le
Assistant Examiner—Lisa V. Cook
(74) Attorney, Agent, or Firm—Armstrong, Kratz, Quintos, Hanson & Brooks, LLP

(57) ABSTRACT

An increased risk of a fetal chromosomal abnormality, for example, fetal Down syndrome can be detected by separating or discriminating α-fetoproteins present in the body fluid of a pregnant woman, and measuring the proportion of one or more of the α-fetoproteins which have a specific sugar chain structure, relative to the total α-fetoproteins.

12 Claims, 2 Drawing Sheets

PROCESS FOR DETECTING INCREASED RISK OF FETAL CHROMOSOMAL ABNORMALITY

BACKGROUND OF THE INVENTION

This application claims priority under 35 U.S.C. 119 of Japanese Patent application No. 10-038186, filed Feb. 3, 1998.

This invention provides a simpler process for detecting an increased risk of a fetal chromosomal abnormality, in particular, a simpler process for detecting an increased risk of fetal Down syndrome.

Down syndrome is widely known as a fetal chromosomal abnormality syndrome. The chromosomal abnormality in the case of Down syndrome is an autosomal abnormality and is classified into 21-trisomy type having three 21th chromosomes, 21th-chromosomal translocation type, and mosaic type. The percentages of these types are 95%, 4% and 1%, respectively. Clinical symptoms of Down syndrome are often a typical and characteristic face, a retardation of physical development and a serious mental handicap.

For prenatal diagnosis of Down syndrome, there is generally employed, for example, a method of carrying out amniocentesis in 10 to 20 weeks of gestation, analyzing the chromosomes of cells, and thereby diagnosing whether the fetus has 21-trisomy or not. However, the amniocentesis has a high diagnostic efficiency but is disadvantageous in that it causes abortion with a probability of 0.5 to 1%. There are also methods such as ultrasonic diagnosis and villus examination, but they involves problems such as low reliability and possibility of injury upon a fetus, respectively. In addition, there have been developed various screening methods practiced on the basis of the measurement of the maternal blood components. In particular, there is widely employed a method comprising calculating the degree of risk from the maternal age and the concentrations of α-fetoprotein (AFP), human chorionic gonadotropin (hCG) and unconjugated estriol (uE3) in the maternal blood (Wald N J. Densem J W. Smith D. Klee G G: Four-Marker Serum Screening For Down's syndrome. Prenat. Diagn. 1994; 14: 707–716). Further, for example, Japanese Patent Application Kohyo No. 8-500181 discloses a process comprising drying the maternal blood of a pregnant woman and then comparing its hCG level with a reference standard value and a process co-using an AFP level value. Japanese Patent No. 2525474 discloses a process for measuring the contents of uE3, progesterone, 16 α-hydroxydehydroepiandrosterone and the like in a maternal serum sample wherein AFP is also measured. JP-A 2-5895 discloses, for example, a process for measuring the concentration of SOD-1 in an extra-cellular body fluid such as the serum, amniotic fluid or the like of a pregnant woman. However, the above processes involve, for example, the following problems: analysis of the measurement results is troublesome, the sensitivity is still as low as 60 to 70%, and the measurement results tend to be affected by maternal conditions such as the body weight, the contraction of diabetes, habit of smoking, etc.

BRIEF SUMMARY OF THE INVENTION

The present invention has been accomplished in view of such circumstances as above, and an object of the present invention is to provide a process for detecting an increased risk of a fetal chromosomal abnormality which is excellent in harmlessness to a pregnant woman and her fetus and has a high reliability of examination results, and a reagent or kit used in said process.

The present invention provides a process for detecting an increased risk of a fetal chromosomal abnormality which comprises separating AFPs present in a body fluid of a pregnant woman on the basis of the difference between or among their sugar chain structures, measuring one or more of AFPs having a specific sugar chain structure, and detecting the increased risk on the basis of a result of the measurement.

The present invention also provides a reagent for detecting an increased risk of a fetal chromosomal abnormality, which comprises a protein capable of recognizing a specific sugar chain of at least one of AFPs and is used for separating AFPs.

The present invention further provides a process for detecting an increased risk of fetal chromosomal abnormality which comprises separating AFPs present in the body fluid of a pregnant woman on the basis of the difference between or among their sugar chain structures, measuring the proportion of one or more of the AFPs which have a specific sugar chain structure, relative to the total AFPs, and detecting the increased risk on the basis of a result of the measurement.

The present invention also provides a kit for detecting an increased risk of a fetal chromosomal abnormality which comprises (1) a lectin capable of recognizing a specific sugar chain of at least one of AFPs and (2) an anti-AFP antibody.

The present invention further provides as kit for detecting an increased risk of a fetal chromosomal abnormality which comprises (1) a lectin capable of recognizing a specific sugar chain of at least one of AFPs, (2) an anti-AFP antibody capable of binding to all AFPs irrespective of whether the lectin binds to AFPs or not and (3) an anti-AFP antibody having a low reactivity with an AFP having the lectin attached thereto but having high reactivity with an AFP to which the lectin does not bind.

DETAILED DESCRIPTION OF THE INVENTION

In order to establish a process for detecting an increased risk of a fetal chromosomal abnormality which has no undesirable influence on a pregnant woman and her fetus, has a high reliability of examination results and is simple, the present inventors have earnestly investigated to reach such finding that an increased risk of a fetal chromosomal abnormality can be detected with high reliability by measuring one or more of AFPs having a specific sugar chain structure which are present in the body fluid of a pregnant woman, and on the basis of this finding, the present invention has been accomplished.

AFP is a carcinoembryonic glycoprotein produced in fetal liver or malignant tumors such as hepatocellular carcinoma and yolk sac tumor and is often used as an important indication for diagnoses of various liver diseases.

In general, AFP has an asparagine-linked type (N-glycoside type) bi-antennarly complex type sugar chain per molecule. Therefore, two or more forms of AFPs can be separated as AFPs having different sugar chains by a method in which AFP bands separated by affinity electrophoresis using a lectin having different affinities for different oligosaccharides are detected by an antibody affinity blotting method. For example, when concanavalin A (Con A) is used, AFPs are separated as AFP-C1 and AFP-C2 on the basis of the kinds of their sugar chains. When *Lens culinaris* agglutinin (LCA) is used, AFPs are separated as AFP-L1, AFP-L2 and AFP-L3. When erythroagglutinating phytohemagglutinin-E4 (PHA-E4) is used, AFPs are separated as AFP-P1 to AFP-P5, and AFP-P3f having a faster mobility than AFP-P3 also appears. When *Coleopteron grub* agglutinin (alloA) is used, AFPs are separated as AFP-A1, AFP-A2 and AFP-A3, and AFP-A1s having a slower mobility than AFP-A1 appears in some cases. When *Ricinus communis* agglutinin (RCA-120) is used, AFPs are separated as AFP-R1, AFP-R2 and AFP-R3, and AFP-R1f having a faster mobility than AFP-R1 appears in some cases. When *Datura stramonium* agglutinin (DSA) is used, AFPs are separated as AFP-D1 to AFP-D6. When *Aleuria aurantia* agglutinin (AAL) is used, AFPs are separated as AFP-AA1 to AFP-AA4 (Kazuhisa Taketa "Clinical Examination" vol. 39, No. 1, pp. 66–70 (1995), Shimizu K., Clin. Chim. Acta., 254, 23–40 (1996)).

It is known that during the gestation, amniotic fluid and maternal serum have a high AFP level. This is because AFPs are produced in immature fetal liver. That is, in the initial fetal life, an AFP having a fucosylated core N-acetylglucosamine (GlcNAc) residue and monosialo-AFP having an exposed galactose (Gal) residue on the mannose (Man) α1→6 branch side are produced in liver in relatively large amounts. An AFP having bisect type GlcNAc appears in amniotic fluid in the eary stages of gestation. With the growth of the fetus and the maturation of the liver, the amount of AFPs produced decreases. On the other hand, since the serum AFP concentration of an adult is usually 10 ng/ml or less, it is conjectured that a large portion of AFPs which appear in the maternal serum during gestation is produced by the fetus.

Preferable examples of the AFP(s) according to the present invention are those having a specific sugar chain structure. The specific sugar chain structure includes, for example, the following:

1. A Bi-antennarly complex type sugar chain of the formula [1]:

2. Sugar Chain Structures Formed by the Conversion of the Bi-antennarly Complex Type Sugar Chain ① Sugar Chain Structures Formed by the Addition of a Sugar i) Sugar Chain Structures Formed by Adding Fucose to GlcNAc at the Reducing End by an α1→6 Linkage A specific example thereof is a sugar chain structure of the formula [2]:

ii) Sugar Chain Structures Formed by Adding GlcNAc to Man having α1→6, α1→3 and β1→4 linkages, by a β1→4 linkage A specific example thereof is a sugar chain structure of the formula [3]:

iii) Triple or Quadruple Chain Structures Formed by the Addition of a Sugar Chain to Man Having β1→2 and α1→6 Linkages and/or Man Having β1→2 and α1→3 Linkages.

② Sugar Chain Structures Formed by the Removal of a Sugar Residue i) Sugar Chain Structures Which are Devoid of the Terminal Sialic Acid Residue Specific examples thereof are sugar chain structures of the following formulae [4] to [7]:

ii) Sugar Chain Structures Which are Devoid of Gal at the Non-reducing End A specific example thereof is a sugar chain structure of the formula [8]:

③ Sugar Chain Structures Formed by the Addition of a Sugar and the Removal of a Sugar Residue A specific example thereof is a sugar chain structure of the formula [9]:

④ Sugar Chain Structure Formed by a Change in the Mode of Binding of the Terminal Sialic Acid Residue (the Change of Usual Addition by an α2→6 Linkage to Addition by an α2→3 Linkage)

A specific example thereof is a sugar chain structure of the formula [10]:

The AFP with a specific sugar chain structure according to the present invention also includes AFPs can be separated by use of various lectins. Specific examples thereof are AFP-C1 and AFP-C2 which can be separated by use of Con A; AFP-L1, AFP-L2 and AFP-L3 which can be separated by use of LCA; AFP-P1, AFP-P2, AFP-P3, AFP-P4, AFP-P5 and AFP-P3f which can be separated by use of PHA-E4; AFP-A1, AFP-A2, AFP-A3 and AFP-A1s which can be separated by use of alloA; AFP-R1, AFP-R2, AFP-R3, AFP-R1f and AFP-R3f which can be separated by use of RCA-120; AFP-D1, AFP-D2, AFP-D3, AFP-D4, AFP-D5, AFP-D6 and AFP-D7 which can be separated by use of DSA; and AFP-AA1, AFP-AA2, AFP-AA3 and AFP-AA4 which can be separated by use of AAL. The AFPs and lectins are not limited to them.

When separated by use of a lectin, an AFP having the bi-antennarly complex type sugar chain of the formula [1] as a sugar chain structure is separated as, for example, AFP-C2, AFP-L2, AFP-P2, AFP-A3, AFP-R1 or the like. An AFP having the sugar chain structure of the formula [2] is separated as AFP-C2, AFP-L3, AFP-P2, AFP-A3, AFP-R1 or the like. An AFP having any of the sugar chain structures of the formulae [3], [4] and [9] is separated as AFP-C1, AFP-P5, AFP-A3, AFP-R3 or the like. An AFP having the sugar chain structure of the formula [5] is separated as AFP-C2, AFP-P4, AFP-A3, AFP-R2 or the like. An AFP having the sugar chain structure of the formula [6] is separated as AFP-C2, AFP-P4 or the like. An AFP having any of the sugar chain structures of the formulae [7] and [8] is separated as AFP-C2, AFP-P3, AFP-A3 or the like. An AFP having the sugar chain structure of the formula [10] is separated as AFP-C2, AFP-P5, AFP-A3, AFP-R1 or the like. When separated by use of a lectin other than the above-exemplified lectins, the AFPs are separated as various fractions, depending on properties of the lectin used.

When the AFP(s) having a specific sugar chain structure is measured, the AFP(s) may be measured after previous treatment thereof with glycosyl hydrolase such as sialidase, N-acetyl hexosaminidase, galactosidase, fucosidase or the like.

For example, when an autosomal abnormality (e.g. 18-trisomy or 21-trisomy=Down syndrome) is detected, preferable examples of the AFP having a specific sugar chain structure are AFPs separable by use of a lectin such as LCA, PHA-E4, Con A or the like, among the above-exemplified AFPs having a specific sugar chain structure. More preferable examples thereof are AFP-L2, AFP-L3, AFP-P4, AFP-P5, AFP-C1, etc. When a sex chromosomal abnormality is detected, preferable examples of the AFP having a specific sugar chain structure are AFPs separable by use of LCA or the like, and more preferable examples thereof are AFP-L2, AFP-L3, etc.

As the maternal body fluid used as a sample for measurement in the present invention, amniotic fluid, plasma, serum, etc. can be exemplified. As the maternal body fluid, there is usually used a body fluid collected from a pregnant woman in the 10 to 20 weeks of gestation.

As the protein capable of recognizing the sugar chain structure or vicinity thereof of the AFP(s) having the specific sugar chain structure which is used in the present invention, there can be exemplified lectins, antibodies, etc. The lectins include, for example, Con A, LCA, alloA, RCA-120, DSA, AAL, PHA-E4, *Pisum sativum* agglutinin, *Arachis hypogaca* agglutinin, *Triticum vulgaris* agglutinin, etc. These lectins are properly chosen depending on the specific sugar chain structure of the AFP(s) to be measured. Among them, LCA, PHA-E4 and concanavalin A are preferable.

The antibodies are not particularly limited and any antibody may be used so long as it is an antibody against the specific sugar chain structure or vicinity thereof of the AFP(s). The antibodies may be either polyclonal or monoclonal and may be used singly or in proper combination. In view of the specificity of an antibody having uniform properties, a monoclonal antibody is preferable to a polyclonal antibody. If necessary, these antibodies may be used after being digested with an enzyme such as pepsin or papain into F(ab')2, Fab' or Fab. The antibodies may be used after introducing thereinto any of various substances, for example, labeling substances such as enzymes [e.g. alkaline phosphatases, β-galactosidase, peroxidase, microperoxidase, glucose oxidase, glucose-6-phosphate dehydrogenase, acetylcholinesterase, malate dehydrogenase, luciferase, etc., which are used, for example, in enzyme immunoassay (EIA)], radioisotopes [e.g. $^{99m}$Tc, $^{131}$I, $^{125}$I, $^{14}$C, $^{3}$H, etc., which are used, for example, in radioimmunoassay (RIA)], substances which can emit fluorescence [e.g. fluorescein, dansyl residue, fluorescamine, coumarin, naphthylamine, derivatives thereof, etc., which are used, for example, in fluoro-immunoassay (FIA)], luminescent substances [e.g. luciferin, isoluminol, luminol, bis (2,4,6-trifluorophenyl)oxalate, etc.], substances which can absorb an ultraviolet light [e.g. phenol, naphthol, anthracene, derivatives thereof, etc.], and substances having properties as spin labels, which are represented by compounds having an oxyl group [e.g. 4-amino-2,2,6,6-tetramethylpiperidin-1-oxyl, 3-amino-2,2,5,5-tetramethylpyrrolidin-1-oxyl, 2,6-di-t-butyl-α-(3,5-di-t-butyl-4-oxo-2,5-cyclohexadien-1-ylidene)-p-tolyloxyl, etc.]; and substances having such a property that in the separation of an antigen-antibody complex by high-pressure liquid chromatography (HPLC) or the like, the substances permit stricter separation of said complex from other components by changing properties of said complex, such as molecular weight, hydrophobicity, isoelectric point, etc. (said substance is hereinafter abbreviated as "separation-improving substance"), specific examples of the separation-improving substance being proteins (e.g. α-chymotrypsinogen, β-galactosidase, lysozyme, cytochrome c, trypsin inhibitor, etc.), peptides containing amino acids such as phenylalanine, proline, arginine, lysine, aspartic acid, glutamic acid, etc., halogen atoms [e.g. bromine, chlorine, iodine, etc.], synthetic polymers [e.g. polyethylene glycol, etc.], polyamino acids [e.g. polyglutamic acid, polyaspartic acid, polylysin, polyarginine, polyphenylalanine, polytyrosine, etc.], the poly-peptides having at least three residues derived from a strong acid such as sulfuric acid, phosphoric acid or the like, which have been disclosed, for example, in JP-A 9-301995, alkyl chains having 3 to 10 carbon atoms, fatty acids (e.g. palmitic acid, oleic acid, stearic acid, etc.), and chemical substances which have a reactive group capable of binding to the above-mentioned antibody and have hydrophobicity or ionicity [e.g. N-($\epsilon$-maleimidocaproyloxy)succinimide (EMCS), N-succinimidyl-6-maleimidohexanoate, bismaleimidohexane (BMH), octylamine, etc.].

Specific examples of method for measuring one or more AFPs having a specific sugar chain structure in the present invention are methods using a protein capable of recognizing the specific sugar chain structure of at least one of the AFPs (e.g. a lectin or an antibody). More specific examples thereof are a conventional lectin affinity electrophoresis method using an anti-AFP antibody and a lectin as a protein capable of recognizing the specific sugar chain structure of at least one AFP, a method using a lectin affinity column chromatography, a method using a high-pressure liquid chromatography (HPLC), etc. Since various kits for these conventional methods are on the market, the measurement may be carried out using any of the kits.

The lectin affinity electrophoresis method is practiced, for example, as follows. First, a sample is electrophoresed on a gel containing the lectin capable of recognizing the specific sugar chain structure of at least one AFP, to obtain fractions of AFPs. Then, the gel is treated with the anti-AFP antibody and an enzyme-labeled antibody, against the anti-AFP antibody. After the washing treatment, the gal is treated with a solution containing substrate(s) of the enzyme which produce(s) a dye by the reaction with the enzyme. Then, the gel is subjected to the washing treatment, and the absorption due to each fraction is measured with a densitometer or the like. The percentage of the peak area of each AFP fraction based on the total peak area of the AFP fractions is calculated as the percentage (%) of the AFP fraction.

The method using HPLC is practiced, for example, as follows. There are used a lectin and antibodies different in AFP-recognition site which have a labeling substance (e.g. an enzyme) or a separation-improving substance, respectively, attached thereto. First, a sample is reacted with a lectin capable of recognizing a specific sugar chain structure of at least one of AFPs and the antibody capable of binding to all AFPs irrespective of whether the lectin bonds to AFPs or not, and having the labeling substance attached thereto, and then with the antibody having a low reactivity with AFP(s) having the lectin attached thereto but having a high reactivity with AFP(s) to which the lectin does not bind, and having the separation-improving substance attached thereto. Thereafter, HPLC is carried out to obtain fractions of AFPs. The labeling substance is measured and the percentage of the peak area of each AFP fraction based on the total peak area of the AFP fractions is calculated as the percentage (%) of the AFP fraction.

An outline of the measuring method using lectin affinity electrophoresis is concretely explained below by taking the case of, for example, a method for measuring AFP-L3 by use of AFP-L3 Test Wako (available from Wako Pure Chemical Industries, Ltd.), a kit for measuring AFP-5 L3.

First, a sample is electrophoresed on, for example, an agarose gel containing LCA to obtain fractions of AFPs. The agarose gel is covered with a film having a monoclonal anti-human AFP mouse antibody precoated thereto to carry out the antigen-antibody reaction. Thus, the AFP fractions are transferred onto the antibody-precoated film. The antibody-precoated film is peeled from the agarose gell and washed. Then, the film is immersed in an anti-human AFP rabbit antibody to cause immunoreaction. Subsequently, after the washing treatment, the film is immersed in a peroxidase (POD)-labeled anti-rabbit IgG goat antibody solution. After completion of the reaction and the next washing treatment, the antibody-precoated film is immersed in a color producing reagent solution to be stained. After the staining and the next washing treatment, the absorption of the film is measured at a measuring wavelength of 550 to 650 nm with a densitometer. The percentage (%) of AFP-L3 fraction is calculated by calculating the area of each peak from a densitogram and calculating the percentage of the peak area of the AFP-L3 fraction based on the total peak area of the AFP fractions.

Specifically, the measuring method using HPLC is practiced according to, for example, the process disclosed in JP-A 9-301995, the disclosure of which is hereby incorporated by reference. The measuring method is explained below by taking the case of a method for measuring AFP-L3. A labeling substance such as an enzyme (e.g. POD) or a separation-improving substance such as 4-(p-maleimidophenyl)butyrylAla-(Tyr(SO$_3$H))$_5$ or 4-(p-maleimidophenyl)butyrylAla-(Tyr(SO$_3$H))$_8$ is introduced to Fab' obtained from each of three anti-AFP monoclonal antibodies different in AFP-recognition site, to prepare Fab'-1-POD, Fab'-2-Ala-(Tyr(SO$_3$H))$_5$ and Fab'-3-Ala-(Tyr(SO$_3$H))$_8$. A sample is reacted with Fab'-1-POD and LCA and then with Fab'-2-Ala-(Tyr(SO$_3$H))$_5$ and Fab'-3-Ala-(Tyr(SO$_3$H))$_8$. Of these Fab' fragments, Fab'-3 has a low reactivity with an AFP having LCA attached thereto but has a high reactivity with an AFP for which LCA has no affinity (to which LCA does not bind). Fab'-1 and Fab'-2 have a reactivity of binding to all AFPs irrespective of whether LCA is bound to the AFPs or not. Therefore, in the reaction solution, there are produced two immune complexes, i.e., an immune complex of an AFP for which LCA has affinity, Fab'-2-Ala-(Tyr(SO$_3$H))$_5$ and Fab'-1-POD, and an immune complex of an AFP for which LCA has no affinity (to which LCA does not bind), Fab'-2-Ala-(Tyr(SO$_3$H))$_5$, Fab'-3-Ala-(Tyr(SO$_3$H))$_8$ and Fab'-1-POD. Then, the two complexes were separated on the basis of the number of sulfate residues contained therein, by an anion-exchange chromatography, and the POD activity of each peak is measured. Since the total area of peaks due to the two immune complexes corresponds to the total AFP amount, the percentage (%) of AFP-L3 fraction can be calculated by dividing the peak area of the AFP for which LCA has affinity by the total peak area of AFP fractions.

The number of AFPs to be measured may be either one or two or more.

For detecting an increased risk of a fetal chromosomal abnormality, the measurement is carried out using samples obtained from pregnant women (normal women) who are at substantially the same age and number of gestation weeks as those of pregnant women to be detected and whose fetuses have been confirmed to have no chromosomal abnormality, by amniocentesis, by using the process of the present invention which comprises separating AFPs present in the body fluid of a pregnant woman on the basis of the difference between or among their sugar chain structures, measuring one or more of AFPs having a specific sugar chain structure. Using the thus obtained amount(s) of specific AFP(s) as a reference standard, the amount(s) of specific AFP(s) obtained from a sample to be detected in the same manner as above is compared with the reference standard amount. When there is a significant difference between these two amounts, it is diagnosed that the sample is a positive one.

For detecting an increased risk of a fetal chromosomal abnormality, the measurement is also carried out using samples obtained from pregnant women (normal pregnant women) who are at substantially the same age and number of gestation weeks as those of pregnant women to be detected and whose fetuses have been confirmed to have no chromosomal abnormality, by amniocentesis by using the process of the present invention which comprises separating AFPs present in the body fluid of a pregnant woman on the basis of the difference between or among their sugar chain structures, measuring the proportion of one or more of the AFPs which have a specific sugar chain structure, relative to the total AFPs. Using the thus obtained percentage value (proportion) of fraction of a predetermined AFP as a reference standard, a percentage value of fraction of the predetermined AFP obtained from a sample to be detected in the same manner as above is compared with the reference standard value. When there is a significant difference between these two values, it is diagnosed that the sample is a positive one (one having an increased risk of a fetal chromosomal abnormality). A higher or lower percentage value of a fraction of the predetermined AFP than the reference standard value is considered as an indication of a positive one, depending on the kind of AFP(s) to be measured and the kind of the sample. For example, when the detection of an increased risk of fetal Down syndrome is carried out on the basis of the percentage of AFP(L2+L3) fraction, the percentage is significantly higher in the serum and amniotic fluid of a patient than in those of the normal group. When the detection is carried out on the basis of the percentage of AFP-C1 fraction, the percentage is significantly lower in the serum of the patient than in that of the normal group. When the detection is carried out on the basis of the percentage of AFP(P4+P5) fraction or AFP-P4 fraction, the percentage is significantly lower in the amniotic fluid of the patient than in that of the normal group. When the detection of an increased risk of a sex chromosomal abnormality is carried out on the basis of the percentage of AFP(L2+L3) fraction, the percentage is significantly lower in the amniotic fluid of a patient than in that of the normal group.

The reagent for detecting an increased risk of a fetal chromosomal abnormality of the present invention contains a protein capable of recognizing the specific sugar chain structure of at least one AFP, such as an antibody or a lectin. Preferable properties and specific examples of the constituents of the reagent are as described above.

The kit for detecting a fetal chromosomal abnormality of the present invention contains (1) a lectin capable of recognizing a specific sugar chain of at least one of AFPs and (2) an anti-AFP antibody.

The kit for detecting a fetal chromosomal abnormality of the present invention also contains (1) a lectin capable of recognizing a specific sugar chain of at least one of AFPs, (2) an anti-AFP antibody capable of binding to all AFPs irrespective of whether the lectin binds to AFPs or not and (3) an anti-AFP antibody having a low reactivity with an AFP having the lectin attached thereto but having high reactivity with an AFP to which the lectin does not bind.

More specific examples thereof are kits for lectin affinity electrophoresis which contain an agarose gel containing a predetermined lectin, a film having an anti-human AFP antibody precoated thereto, a solution containing another anti-AFP antibody (a second anti-AFP antibody), a solution of an antibody against the second anti-human AFP antibody which has been labeled with an enzyme such as POD, a coloring producing reagent solution [e.g. reduced form β-nicotinamide adenine dinucleotide and Nitrotetrazolium Blue (Nitro-TB) in the case where the labeling enzyme is POD], an aqueous hydrogen peroxide solution, a wash liquid, etc.; and kits for measuring one or more AFPs using a column containing an agarose gel containing a lectin such as LCA, an anti-AFP antibody-1 having a separation-improving substance [e.g. Ala-(Tyr($SO_3H$))$_5$ or Ala-(Tyr($SO_3H$))$_8$] introduced thereto, an anti-AFP antibody-2 labeled with an enzyme such as POD, an anti-AFP antibody-3 having as a substance attached thereto a separation-improving substance different from that attached to the anti-AFP antibody-1, a substrate solution (containing 4-acetamidophenol, an aqueous hydrogen peroxide solution, etc. in the case of using POD as the antibody-labeling substance) wherein the anti-AFP antibody-1 and the anti-AFP antibody-2 have a reactivity of binding to all AFPs irrespective of whether the lectin is bound to the AFPs or not, and the anti-AFP antibody-3 has a low reactivity with AFP(s) having the lectin attached thereto but a high reactivity with AFP(s) for which the lectin has no affinity (to which the lectin does not bind).

Preferable properties and specific examples of the constituents of the kits are as described above.

The reagents contained in the above-exemplified kits may contain other reagents usually used in the art, such as buffers, reaction accelerators, sugars, proteins, salts, stabilizers (e.g. surfactants), antiseptics, etc., which neither deteriorate the stability of reagents present together with them nor inhibit the reaction of the AFP(s) with the lectin (or antibody). The concentrations of the other reagents may be properly chosen in concentration ranges usually employed in the art.

It is well known that metal ions such as magnesium ions affect the activity and stability of lectins. The kits may contain such metal ions.

As the buffers usable in the reagent or kit of the present invention, there can be exemplified all buffers usually used in immunoturbidimetry, immunonephelometry, radioimmunoassay and enzyme immunoassay, such as Tris buffers, phosphate buffers, veronal buffers, borate buffers, Good's buffers, etc. The pH at the reaction for measurement is not particularly limited so long as it does not inhibit the antigen-antibody reaction. Usually, the pH is preferably chosen in the range of 6 to 10.

The present invention is explained below in further detail with reference to Examples, which are not by way of limitation but by way of illustration.

EXAMPLE 1

AFPs in maternal serum and amniotic fluid in the case of fetal Down syndrome
(1) Samples There were used the sera and amniotic fluids in the 15 to 19 weeks of gestation of 17 pregnant women of 27 to 44 years old who had been confirmed to have a fetus with Down syndrome, by amniocentesis.

As reference samples, there were used the sera and amniotic fluids of 20 normal pregnant women who were at the same age and number of gestational weeks as those of the pregnant women having the fetus with Down syndrome and who had been confirmed to have a fetus having no chromosomal abnormality, by amniocentesis.

(2) Measurement of the Total AFP Amount

The total AFP amount was measured by use of an IMx AFP assay system (Abbot Laboratories, Ill., USA) according to the standard procedure described in the attached document.

(3) Measurement of the Percentages of AFP Fractions

On a 1% agarose gel of 1 mm thick containing a predetermined concentration of a predetemined lectin was applied 2 µl of each serum sample or each amniotic fluid sample diluted with physiological saline to a total AFP concentration of about 50 ng/ml, and electrophoresis was carried out under the conditions described below, to separate one or more AFPs having a specific sugar chain structure (such an AFP is hereinafter abbreviated as "marker"). When DSA or RCA-120 was used as a lectin, each sample was treated with sialidase and then applied on the agarose film.

| Electrophoresis conditions: | |
|---|---|
| Temperature | 7° C. |
| Electrophoresis time | 50 min. |
| Buffer solution | 25 mM barbital/NaOH, pH 8.6 |
| Voltage | constant voltage 200 V. |

Table 1 shows a lectin used for separating each marker and its concentration in the agarose gel.

TABLE 1

| Marker | Lectin used | Lectin concentration (mg/ml) |
|---|---|---|
| L2 + L3 | LCA | 0.2 |
| C1 | ConA | 1.0 |
| P4 + P5 | PHA-E4 | 0.25 |
| P4 | PHA-E4 | 0.25 |
| D2 + D6 + D7 | DSA | 0.4 |
| R3 + R3f | RCA-120 | 0.8 |

The AFP fractions separated were transferred to a nitrocellulose film precoated with a monoclonal anti-AFP mouse antibody, and after washing treatment, they were further reacted with a polyclonal anti-AFP rabbit antibody and a POD-labeled anti-rabbit IgG goat antibody. After washing treatment, the reaction products were reacted with Nitrotetrazolium Blue, NADH, phenol and hydrogen peroxide to subject the AFP fractions to coloration. The peak area of each fraction was measured with a densitometer (580 nm) and the percentage of the fraction was calculated by the following equation:

Fraction percentage (%)=(the peak area of each fraction/the total peak area of the fractions)×100

(4) Results

Table 2 shows, for each marker, the mean±SD obtained from each of the fetal Down syndrome group and the nomal group and the significant difference therein between the two group. As a significant test, Student's t test was employed.

TABLE 2

| | | Mean ± SD | | |
|---|---|---|---|---|
| Sample | Marker | Normal group | Fetal Down syndrome group | Significant difference (P value) |
| Serum | AFP (ng/ml) | 54.5 ± 16.5 | 39.3 ± 17.5 | 0.0107 |
| | L2 + L3 (%) | 35.5 ± 4.4 | 41.8 ± 6.9 | 0.00303 |
| | C1 (%) | 10.5 ± 2.7 | 8.2 ± 4.3 | 0.0636 |
| | P4 + P5 (%) | 30.2 ± 4.1 | 29.7 ± 2.8 | 0.672 |
| | P4 (%) | 18.8 ± 3.0 | 18.5 ± 2.8 | 0.756 |
| Amniotic fluid | AFP (ng/ml) | 16000 ± 6320 | 15900 ± 19000 | 0.983 |
| | L2 + L3 (%) | 41.3 ± 5.0 | 49.4 ± 7.3 | 0.000593 |
| | C1 (%) | 20.8 ± 3.6 | 20.3 ± 6.6 | 0.772 |
| | P4 + P5 (%) | 36.7 ± 4.6 | 32.4 ± 4.6 | 0.00748 |
| | P4 (%) | 20.4 ± 3.2 | 15.4 ± 1.3 | 0.00000120 |
| | D2 + D6 + D7 (%) | 4.4 ± 1.4 | 3.9 ± 1.7 | 0.383 |
| | R3 + R3f (%) | 82.4 ± 4.5 | 80.8 ± 4.8 | 0.293 |

As is clear from Table 2, in serum, the fetal Down syndrome group had a significantly lower value of the total AFP amount and a significantly higher value of the percentage of AFP(L2+L3) fraction than did the normal group. The significant difference between this group and the normal group in the percentage of AFP(L2+L3) fraction is larger than that in the total AFP amount. In addition, although there was no significant difference in the percentage of AFP-C1 fraction because the number of samples was small, it was strongly suggested that the fetal Down syndrome group tends to have a lower value of the percentage of AFP-C1 fraction than does the normal group.

Similarly, in amniotic fluid, the fetal Down syndrome group had a significantly higher value of the percentage of AFP(L2+L3) fraction, a significantly lower value of the percentage of AFP(P4+P5) fraction and a significantly lower value of the percentage of AFP-P4 fraction than did the normal group. The significant differences between this group and the normal group in all of the percentage of AFP(L2+L3) fraction, the percentage of AFP(P4+P5) fraction and the percentage of AFP-P4 fraction were larger than that in the total AFP amount.

Table 3 shows the results of calculating the sensitivity, specificity and diagnostic efficiency by use of the mean±2SD or mean−2SD as a cutoff value, in the case of each marker showing a significant difference in Table 2.

TABLE 3

| Sample | Marker | Cutoff value | Sensitivity | Specificity | Diagnostic efficiency |
|---|---|---|---|---|---|
| Serum | AFP (ng/ml) | 21.5 ng/ml or less | 11.8% | 100% | 59.5% |
| | L2 + L3 (%) | 44.2% or more | 41.2% | 100% | 73.0% |
| Amniotic fluid | L2 + L3 (%) | 51.2% or more | 41.2% | 100% | 73.0% |
| | P4 + P5 (%) | 27.5% or less | 11.8% | 100% | 59.5% |
| | P4 (%) | 14.0% or less | 11.8% | 100% | 59.5% |

As is clear from Table 3, the diagnostic efficiency of AFP(L2+L3) fraction in each of serum and amniotic fluid was 73% which was the highest. Thus, it was confirmed that the AFP(L2+L3) fraction is very useful for detecting an increased risk of fetal Down syndrome. In other words, it was confirmed. that AFPs having fucose added to GlcNAc at the reducing end of the sugar chain by α1→6 linkage is effective in the detection of the increased risk of fetal Down syndrome.

EXAMPLE 2

The percentage of AFP(L2+L3) fraction in maternal sera and amniotic fluids of a fetal chromosomal abnormality group and a normal group (1) Samples There were used the sera and amniotic fluids in the 15 to 19 weeks of gestation of pregnant women of 24 to 44 years old who had been confirmed to have a fetus having 21-trisomy or 18-trisomy autosomal abnormality or a sex chromosomal abnormality, by amniocentesis.

As reference samples, there were used the sera and amniotic fluids of normal pregnant women who were at the same age and number of gestational weeks as those of the pregnant women having the fetus having 21-trisomy or 18-trisomy and who had been confirmed to have a fetus having no chromosomal abnormality, by amniocentesis.

(2) Measurement of the Percentage of AFP(L2+L3) Fraction

AFP fractions were separated by use of AFP-L3 Test Wako (available from Wako Pure Chemical Industries, Ltd.) according to the standard procedure described in the attached document. The peak area of each AFP fraction was measured with a densitometer (580 nm) and the percentage of AFP(L2+L3) fraction was calculated in the same manner as described in Example 1.

(3) Results

Table 4 shows the mean±SD obtained from each group and the significant difference therein from the normal group. As a significant test, Student's t test was employed.

TABLE 4

| Sample | Group | Number of cases | Mean (%) ± SD | Significant difference (P value) |
|---|---|---|---|---|
| Serum | 21-Trisomy (Down syndrome) | 18 | 41.6 ± 6.71 | 0.000202 |
| | 18-Trisomy | 8 | 38.5 ± 8.03 | 0.169 |
| | Sex chromosomal abnormality | 6 | 32.2 ± 5.65 | 0.471 |
| | Normal | 70 | 34.1 ± 5.53 | — |
| Amniotic fluid | 21-Trisomy (Down syndrome) | 18 | 49.6 ± 6.82 | 0.000158 |
| | 18-Trisomy | 10 | 44.4 ± 5.59 | 0.179 |
| | Sex chromosomal abnormality | −7 | 28.2 ± 4.40 | 0.0000653 |
| | Normal | 50 | 41.7 ± 4.61 | — |

As is clear from Table 4, in the 21-trisomy (Down syndrome) group, the percentage of AFP(L2+L3) fraction in each of serum and amniotic fluid was significantly high. In the sex chromosomal abnormality group, the percentage of AFP(L2+L3) fraction in amniotic fluid was significantly low.

Table 5 shows the results of calculating the sensitivity, specificity and diagnostic efficiency by use as a cutoff value the specific percentage of AFP(L2+L3), by which the diagnostic efficiency can be made to maximum, in the case of each group showing a significant difference in Table 4.

TABLE 5

| Sample | Disease | Cutoff value | Sensitivity | Specificity | Diagnostic efficiency |
|---|---|---|---|---|---|
| Serum | 21-Trisomy | 42.0% or more | 50.0% | 95.7% | 86.4% |
| Amniotic fluid | 21-Trisomy | 51.0% or more | 50.0% | 100% | 86.8% |
| | Sex chromosomal abnormality | 29.0% or less | 28.6% | 100% | 91.2% |

As is clear from Table 5, there was confirmed the usefulness of the percentage of AFP(L2+L3) fraction in each of serum and amniotic fluid, in other words, the usefulness of AFPs having fucose added to GlcNAc at the reducing end of the sugar chain by α1→6 linkage, in the detection an increased risk of 21-trisomy or a sex chromosomal abnormality.

EXAMPLE 3

The total AFP amount and the percentage of AFP(L2+L3) fraction in maternal serum in the case of fetal Down syndrome (1) Samples There were used the sera in the 15 to 19 weeks of gestation of 18 pregnant women of 27 to 44 years old who had been confirmed to have a fetus with Down syndrome, by amniocentesis.

As reference samples, there were used the sera of 70 normal pregnant women who were at the same age and number of gestational weeks as those of the pregnant women having the fetus Down syndrome and who had been confirmed to have a fetus having no chromosomal abnormality, by amniocentesis.

(2) Measurement of the Total AFP Amount

The total AFP amount was measured by use of an IMx AFP assay system (Abbott Laboratories, Ill., USA) according to the standard procedure described in the attached document.

(3) Measurement of the Percentage of AFP(L2+L3) Fraction

AFP fractions were separated by use of AFP-L3 Test Wako (available from Wako Pure Chemical Industries, Ltd.) according to the standard procedure described in the attached document. The peak area of each AFP fraction was measured with a densitometer (580 nm) and the percentage of AFP(L2+L3) fraction was calculated in the same manner as described in Example 1. As a significant test, Student's t test was employed.

(4) Results

Figure 1:
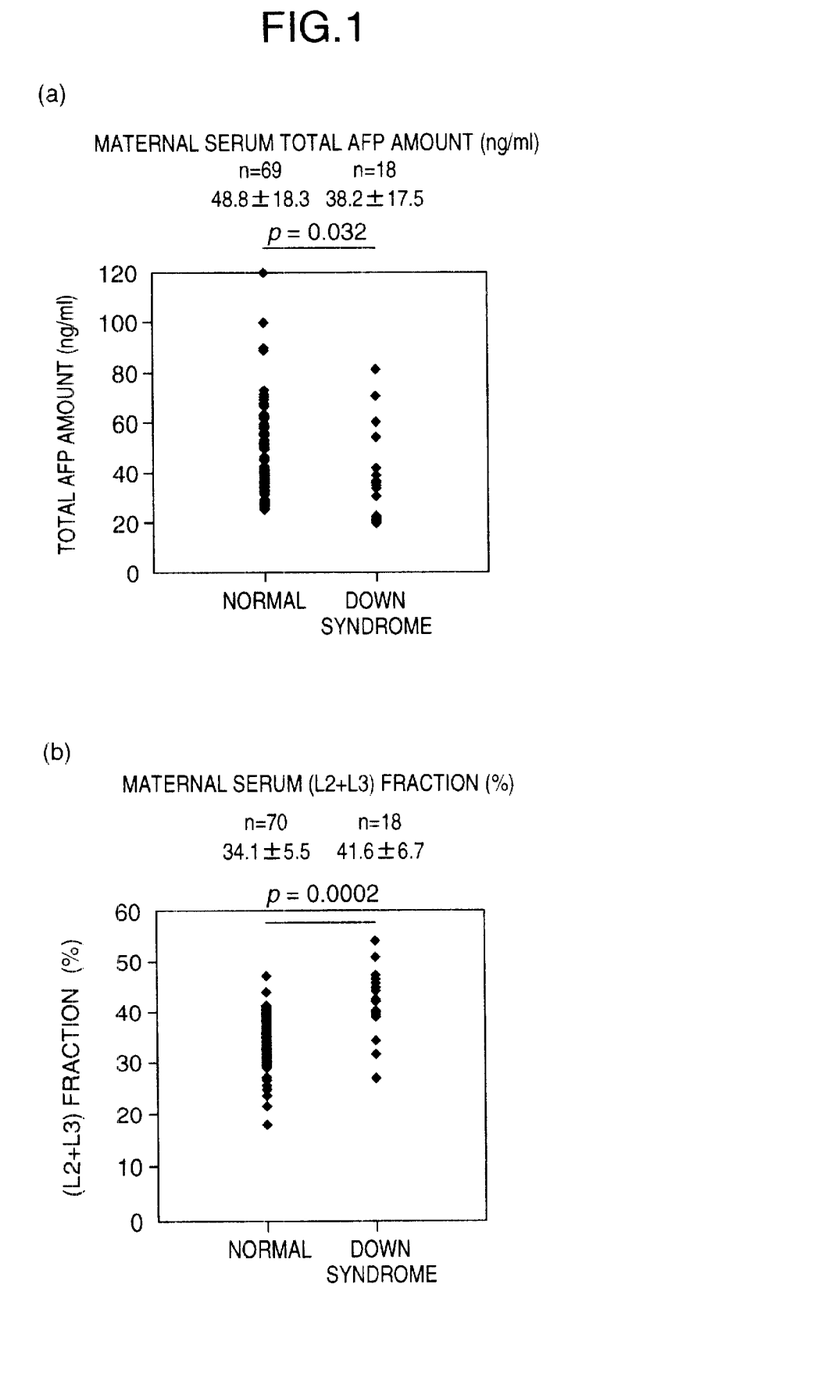
FIG. 1 shows results obtained in Example 3: (a) and (b) show the distributions of the total AFP amount and the percentage of AFP(L2+L3) fraction, respectively, in each of serum samples collected from normal pregnant woman or pregnant woman who were confirmed to have a fetus with fetal Down syndrome.

FIG. 1(a) and FIG. 1(b) show the distributions of the total AFP amount and the percentage of AFP(L2+L3) fraction, respectively, in maternal serum in each of the normal group and the Down syndrome group.

From the results shown in these figures, it can be seen that in both the total AFP amount and the percentage of AFP (L2+L3) fraction, there was a significant difference between the fetal Down syndrome group and the normal group.

Table 6 shows the sensitivity, specificity and diagnostic efficiency of the total AFP amount and the percentage of AFP(L2+L3) fraction which were calculated by taking the cutoff values of the total AFP amount and the percentage of AFP(L2+L3) fraction as 24 ng/ml and 42%, respectively.

TABLE 6

| Marker | Cutoff value | Sensitivity | Specificity | Diagnostic efficiency |
|---|---|---|---|---|
| Total AFP amount | 24 ng/ml or less | 27.8% | 100.0% | 85.1% |
| Percentage of AFP (L2 + L3) fraction | 42% or more | 50.0% | 95.7% | 86.4% |

Figure 2:
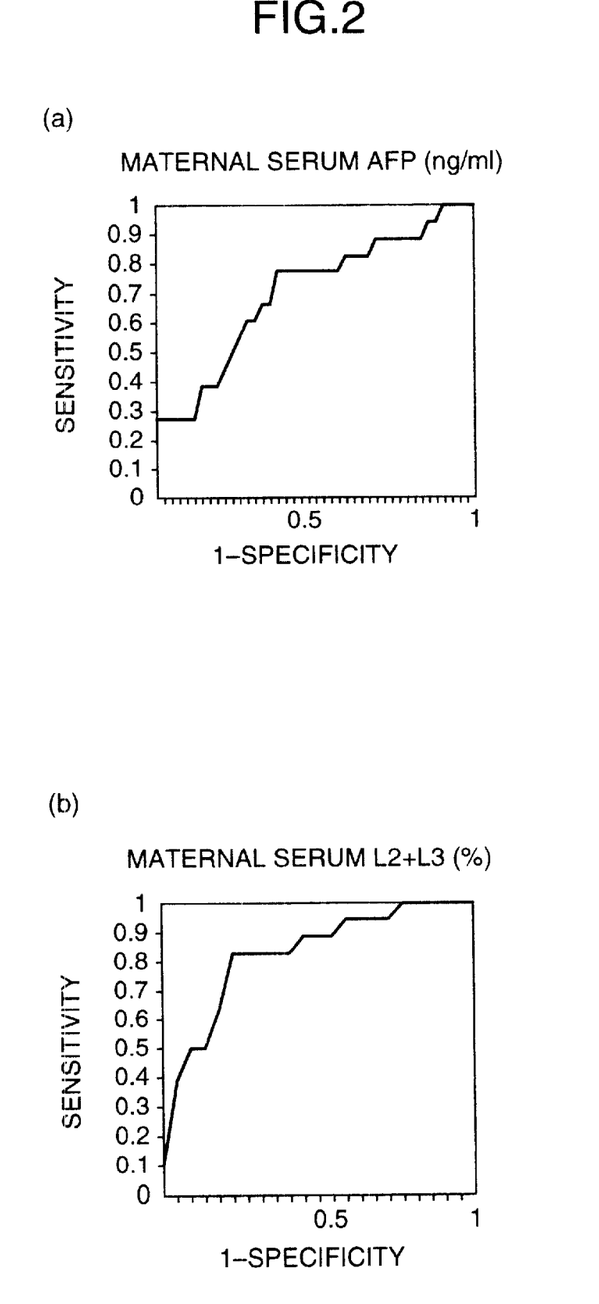
FIG. 2 shows receiver operating characteristic curves obtained on the basis of the results obtained in Example 3: (a) shows a receiver operating characteristic curve obtained on the basis of the results of measuring the total AFP amount, and (b) shows a receiver operating characteristic curve obtained on the basis of the results of measuring the percentage of AFP(L2+L3) fraction.

FIGS. 2(a) and (b) show receiver operating characteristic (ROC) curves in the case of the total AFP amount and the percentage of AFP(L2+L3) fraction, respectively.

On the basis of FIGS. 2(a) and (b), AUC (area under the curve) values were calculated to be 0.700 and 0.835 in the case of the total AFP amount and the percentage of AFP (L2+L3) fraction, respectively. From the above facts, it can be seen that the percentage of AFP(L2+L3) fraction is more useful than the total AFP amount for the detection of the increased risk of Down syndrome and permits exacter diagnosis than does the total AFP amount.

The present invention provides a process, reagent and kit for detecting an increased risk of a fetal chromosomal abnormality which have no undesirable influence on a pregnant woman and her fetus, has a high reliability of examination results and is simple.

What is claimed is:

1. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
   (1) reacting the sample with a lectin or an antibody, which is capable of recognizing the sugar chain structure of the specific α-fetoproteins;
   (2) measuring the amount of α-fetoprotein that is bound to said lectin or antibody, and taking said measured amount as the amount of the specific α-fetoproteins in the sample, and measuring the amount of total α-fetoprotein in the sample; and
   (3) determining that there is an increased risk of fetal chromosomal abnormality when there is:
      a significant difference between the amount of the specific α-fetoproteins obtained in the step (2) with an amount of the specific α-fetoproteins measured in a body fluid sample of a pregnant woman having a normal fetus as a reference standard or a significant difference between a calculated ratio of the amount of the specific α-fetoproteins relative to the amount of total α-fetoprotein with a predetermined ratio from a body fluid sample of a pregnant woman having a normal fetus.

2. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
   (1) reacting the sample with a lectin or an antibody ①, which is capable of recognizing the sugar chain structure of the specific α-fetoprotein, and an antibody ②, which is capable of binding to all α-fetoproteins including the specific α-fetoprotein, the reactions being performed at the same time or first with the lectin or the antibody ① and then with the antibody ②;
   (2) measuring the amount of α-fetoprotein that is bound to the lectin or the antibody ① and the antibody ②, and taking said measured amount as the amount of specific α-fetoprotein in the sample, and measuring the amount of total α-fetoprotein in the sample; and
   (3) determining that there is an increased risk of fetal chromosomal abnormality when there is:
      a significant difference between the amount of the specific α-fetoproteins obtained in step (2) with an amount of the specific α-fetoproteins measured in a body fluid sample of a pregnant woman having a normal fetus as a reference standard or a significant difference between the calculated ratio of the amount of the specific α-fetoproteins relative to the amount of total α-fetoprotein with a predetermined ratio from a body fluid sample of a pregnant woman having a normal fetus.

3. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
   (1) reacting the sample with a lectin or an antibody ①, which is capable of recognizing the sugar chain structure of the specific α-fetoprotein, an antibody ②, which is capable of binding to all α-fetoprotein including the specific α-fetoprotein, and an antibody ③ having a low reactivity with an α-fetoprotein to which the lectin or the antibody ① is attached but having a high reactivity with an α-fetoprotein to which the lectin or the antibody ① is not bound, the reactions being performed at the same time or first with the lectin or the antibody ① and then with the antibody ② and the antibody ③, or first with the lectin or the antibody ① and the antibody ② and then with the antibody ③;
   (2) measuring the amount of α-fetoprotein that is bound to the lectin or the antibody ① and the antibody ②, and taking said measured amount as the amount of specific α-fetoprotein in the sample, and measuring the amount of total α-fetoprotein in the sample; and
   (3) determining that there is an increased risk of fetal chromosomal abnormality when there is:
      a significant difference between the amount of the specific α-fetoproteins obtained from the amount obtained by step (2) with an amount of the specific α-fetoproteins measured in a body fluid sample of a pregnant woman having a normal fetus as a reference standard or
      a significant difference between the calculated ratio of the amount of the specific α-fetoproteins relative to the amount of total α-fetoprotein with a predetermined ratio from a body fluid sample of a pregnant woman having a normal fetus.

4. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
   (1) dividing the sample into a first portion and a second portion;
   (2) measuring an amount of the specific α-fetoproteins in the first portion, the process further comprises:
      (i) reacting the first portion with a lectin or an antibody, which is capable of recognizing the sugar chain structure of the specific α-fetoprotein; and
      (ii) measuring the amount of α-fetoprotein that is bound to the lectin or the antibody, and taking said measured amount as the amount of specific α-fetoprotein in the sample;
   (3) measuring the amount of the total α-fetoprotein of the second portion;
   (4) calculating a ratio of the amount of the specific α-fetoproteins obtained from the amount obtained in step (2)(ii) relative to the amount of total α-fetoprotein; and
   (5) determining an increased risk of fetal chromosomal abnormality by the presence of a significant difference between the calculated ratio with a predetermined ratio from a body fluid sample of a pregnant woman having a normal fetus.

5. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
   (1) dividing the sample into a first portion and a second portion;

(2) measuring an amount of the specific α-fetoproteins in the first portion, the process further comprises:
  (i) reacting the sample with a lectin or an antibody ①, which is capable of recognizing the sugar chain structure of the specific α-fetoprotein, and an antibody ②, which is capable of binding to all α-fetoproteins including the specific α-fetoprotein, the reactions being performed at the same time or first with the lectin or the antibody ① and then with the antibody ②; and
  (ii) measuring the amount of α-fetoprotein that is bound to the lectin or the antibody ① and the antibody ②, and taking said amount as the amount of specific α-fetoprotein in the sample;
(3) measuring the amount of total α-fetoprotein of the second portion;
(4) calculating a ratio of the amount of the specific α-fetoproteins obtained from the amount obtained by step (2)(ii) relative to the amount of total α-fetoprotein; and
(5) determining an increased risk of fetal chromosomal abnormality by the presence of a significant difference between the calculated ratio with a predetermined ratio from a body fluid sample of a pregnant woman having a normal fetus.

6. A process for determining an increased risk of a fetal chromosomal abnormality by analyzing a pregnant woman body fluid sample containing at least one specific α-fetoprotein, which is an α-fetoprotein with a specific sugar chain structure, the process comprising the steps of:
(1) dividing the sample into a first portion and a second portion;
(2) measuring an amount of the specific α-fetoproteins in the first portion, the process comprises:
  (i) reacting the sample with a lectin or an antibody ①, which is capable of recognizing the sugar chain structure of the specific α-fetoprotein, an antibody ②, which is capable of binding to all α-fetoprotein, and an antibody ③ having a low reactivity with an α-fetoprotein to which the lectin or the antibody ① attached but having a high reactivity with the α-fetoprotein which the lectin or the antibody ① does not bind, the reactions being performed at the same time, or first with the lectin or the antibody ① and then with the antibody ② and the antibody ③, or first with the lectin or the antibody ① and the antibody ② and then with the antibody ③; and
  (ii) measuring the amount of α-fetoprotein that is bound to the lectin or the antibody ① and the antibody ②, and taking said measured amount as the amount of specific α-fetoprotein in the sample; and
(3) measuring the amount of total α-fetoprotein of the second portion;
(4) calculating a ratio of the amount of the specific α-fetoproteins obtained from the amount obtained in step (2)(ii) relative to the amount of total α-fetoprotein; and
(5) determining an increased risk of fetal chromosomal abnormality by the presence of a significant difference between the calculated ratio with a predetermined ratio from a body fluid sample of a pregnant woman having a normal fetus.

7. A process according to any one of claims 1–6, wherein the specific sugar chain structure is one having a bi-antennarly complex sugar chain or a sugar chain formed by the conversion of said bi-antennarly complex sugar chain.

8. A process according to any one of claims 1–6, wherein the lectin is Lens culinaris agglutinin, erythroagglutinating phytohemagglutinin-E4 or concanavalin A.

9. A process according to any one of claims 1–6, wherein the chromosomal abnormality is an autosomal abnormality or a sex chromosomal abnormality.

10. A process according to any one of claims 1–6, wherein the body fluid sample is collected from a pregnant woman in the 10 to 20 weeks of gestation.

11. A process according to any one of claims 1–6, wherein the specific α-fetoprotein is separated by a lectin affinity electrophoresis method, a lectin affinity column chromatography, or a high-pressure liquid chromatography.

12. A process according to claim 11, wherein the total α-fetoprotein is the total amount of the α-fetoprotein fractions separated in the separation step.

* * * * *